United States Patent
Shipp

(10) Patent No.: US 9,138,215 B2
(45) Date of Patent: Sep. 22, 2015

(54) VESSEL SEALING DEVICE

(71) Applicant: John I. Shipp, Atlantic Beach, FL (US)

(72) Inventor: John I. Shipp, Atlantic Beach, FL (US)

(73) Assignee: VI Bravoseal, LLC, St. Thomas (VG)

( * ) Notice: Subject to any disclaimer, the term of this patent is extended or adjusted under 35 U.S.C. 154(b) by 371 days.

(21) Appl. No.: 13/746,278

(22) Filed: Jan. 21, 2013

(65) Prior Publication Data

US 2014/0207184 A1 Jul. 24, 2014

(51) Int. Cl.
*A61B 17/08* (2006.01)
*A61B 17/00* (2006.01)
*A61B 19/00* (2006.01)

(52) U.S. Cl.
CPC ... *A61B 17/0057* (2013.01); *A61B 2017/00659* (2013.01); *A61B 2019/307* (2013.01)

(58) Field of Classification Search
USPC .......................................... 606/213
See application file for complete search history.

(56) References Cited

U.S. PATENT DOCUMENTS

| | | | |
|---|---|---|---|
| 5,342,393 A * | 8/1994 | Stack | 606/213 |
| 5,350,399 A | 9/1994 | Erlebacher et al. | |
| 5,620,461 A | 4/1997 | Muijs Van De Moer et al. | |
| 6,022,351 A * | 2/2000 | Bremer et al. | 606/324 |
| 6,045,569 A | 4/2000 | Kensey et al. | |
| 6,090,130 A | 7/2000 | Nash et al. | |
| 7,175,646 B2 | 2/2007 | Brenneman et al. | |
| 7,250,057 B2 | 7/2007 | Forsberg | |
| 7,335,220 B2 | 2/2008 | Khosravi et al. | |
| 7,488,340 B2 | 2/2009 | Kauphusman et al. | |
| 7,597,705 B2 | 10/2009 | Forsberg et al. | |
| 7,618,438 B2 | 11/2009 | White et al. | |
| 7,850,710 B2 | 12/2010 | Huss | |
| 7,931,670 B2 | 4/2011 | Fiehler et al. | |
| 7,988,706 B2 | 8/2011 | Forsberg | |
| 8,029,533 B2 | 10/2011 | Bagaoisan et al. | |
| 8,048,108 B2 | 11/2011 | Sibbitt, Jr. et al. | |
| 8,075,589 B2 | 12/2011 | Pipenhagen et al. | |
| 8,080,034 B2 | 12/2011 | Bates et al. | |
| 8,128,632 B2 | 3/2012 | Paris et al. | |
| 8,128,652 B2 | 3/2012 | Paprocki | |
| 8,128,653 B2 | 3/2012 | McGuckin, Jr. et al. | |
| 2001/0007077 A1 | 7/2001 | Ginn et al. | |
| 2002/0002386 A1 | 1/2002 | Ginn et al. | |
| 2003/0078598 A1 | 4/2003 | Ginn et al. | |
| 2006/0195123 A1 | 8/2006 | Ginn et al. | |
| 2006/0195124 A1 | 8/2006 | Ginn et al. | |
| 2006/0265007 A1 | 11/2006 | White et al. | |
| 2006/0271078 A1 | 11/2006 | Modesitt | |
| 2007/0060895 A1 | 3/2007 | Sibbitt, Jr. et al. | |
| 2007/0185529 A1 * | 8/2007 | Coleman et al. | 606/213 |
| 2008/0109030 A1 | 5/2008 | Houser et al. | |
| 2008/0243182 A1 * | 10/2008 | Bates et al. | 606/213 |
| 2009/0254119 A1 | 10/2009 | Sibbitt, Jr. et al. | |
| 2010/0087854 A1 * | 4/2010 | Stopek et al. | 606/215 |
| 2012/0022585 A1 | 1/2012 | Atanasoska et al. | |

\* cited by examiner

*Primary Examiner* — Tuan V Nguyen

(74) *Attorney, Agent, or Firm* — Michael L. Leetzow, P.A.

(57) ABSTRACT

A seal assembly that seals opening in the wall of a blood vessel has a first sealing element for placing inside the lumen of the blood vessel and to engage the interior wall surface, a shaft integrally formed with the first sealing element and fixed in a predetermined configuration relative to the first sealing element, an outer floating element slidingly movable along the shaft; and a second sealing element, the second sealing element slidingly movable relative to the first sealing element along the shaft to engage the outer floating element and position the outer floating element against the exterior surface and the first sealing element against the interior surface of the blood vessel to seal the opening in the blood vessel.

19 Claims, 14 Drawing Sheets

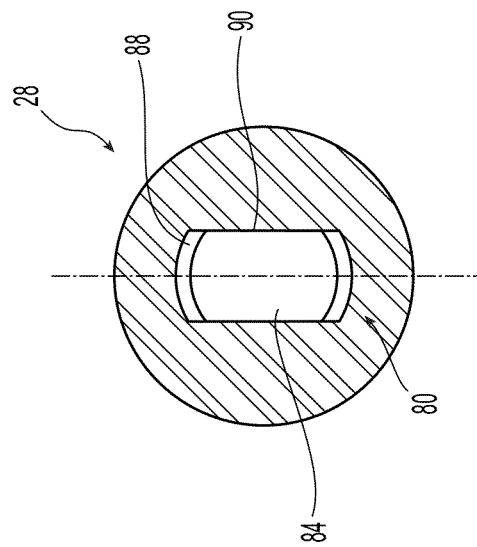
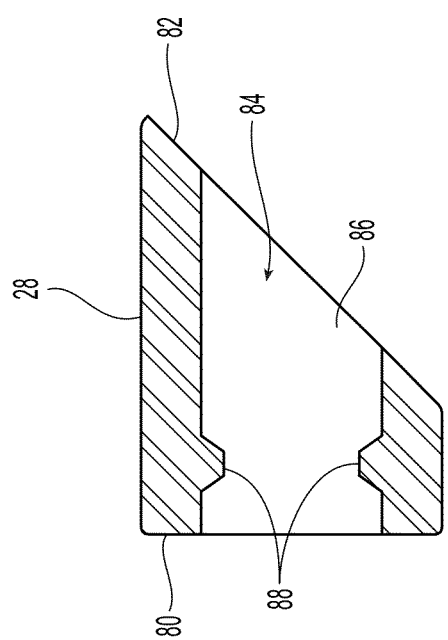
Fig. 4B
Fig. 4A

VESSEL SEALING DEVICE

BACKGROUND OF THE INVENTION

1. Field of the Invention

The present invention relates generally to a sealing device for the closure of puncture holes in blood vessels and, in particular, to a sealing device that does not require a sheath change and is simple to operate.

2. Technical Background

For many diagnostic and interventional procedures it is necessary to access arteries or veins. Vessel access is accomplished either by direct vision or percutaneously. In either case, the target vessel is punctured with a hollow needle containing a tracer wire. When the intravascular positioning of the tracer wire has been verified, the hollow needle is removed leaving the tracer wire. Next, a sheath containing a dilator is pushed in over the tracer wire. The dilator enlarges the puncture opening to facilitate the insertion of the larger diameter sheath into the blood vessel. The sheath usually consists of a hollow tube with an open distal end and a hemostatic valve at a proximal end, which remains outside the body and blood vessel. The hemostatic valve is made of a compliant material and is designed in such a way as to allow devices such as catheters to be inserted and withdrawn from the blood vessel with minimal blood loss. After the sheath has been inserted into the blood vessel, the dilator is removed leaving a clear passageway in the sheath for the catheter. The sheath is removed from the blood vessel after the procedure is finished resulting in bleeding at the puncture site that must be staunched.

Traditionally, pressure is applied at the puncture site to allow the blood to clot, thereby stopping the bleeding. Depending on the amount of anticoagulants that may have been administered to the patient during and prior to the procedure, the time that the pressure must be maintained varies from 15 minutes to more than an hour. Once bleeding has stopped, a pressure bandage is placed over the site of the puncture in an attempt to protect the integrity of the clot. The pressure bandage must remain in place for some time, usually from 8 to 24 hours. During this period of time the patient must remain in bed, sometimes requiring an overnight hospital stay.

To shorten the length of time required for the patient to become ambulatory and to lessen complications that may arise from the traditional method of sealing the opening, several closure devices have been developed. One such device, as described in U.S. Pat. No. 5,620,461, is a foldable sheet with an attachment thread that is inserted into the opening in the blood vessel and an arresting element that is applied over the attachment element against the outside of the blood vessel. Another such device is described in U.S. Pat. Nos. 6,045,569 and 6,090,130, and includes an absorbable collagen plug cinched down against an absorbable intervascular anchor via an absorbable suture. The absorbable intervascular anchor has an elongated rectangular shape that requires it to be inserted into the puncture wound with its longitudinal axis approximately parallel to the sheath axis. This requires it to be rotated ninety degrees after insertion so that blood flow obstruction is minimized. A specially designed sheath is necessary to assure proper rotation, thus resulting in an otherwise unnecessary sheath change. The long dimension of the anchor is thus larger than the cannula inside diameter (ID) and the width is smaller than the ID. The collagen plug is in an elongated state prior to deployment and is forced into a ball shape via a slipknot in the suture, which passes through the collagen, and a tamper that applies a distal force to it. The anchor acts as a support for the suture cinch which forces the collagen ball shape up against the exterior blood vessel wall and the anchor. Blood flow escaping around the anchor is slowed down and absorbed by the collagen material and thus forms a clotting amalgamation outside the blood vessel that is more stable than the traditional method of a standalone clot. The added robustness of the amalgamation clot allows earlier ambulation of the patient.

The device raises several issues. It is not a true sealing device but rather a clotting enhancement device, as opposed to a device with two flat surfaces exerting sealing pressure on both the interior and exterior of the blood vessel, a much more reliable technique. In either case, bleeding occurs during the time between removal of the sheath and full functionality of the deployed device. Thus "instant" sealing pressure from two flat surfaces is desirable over a method that relies to any extent on clotting time. One such device is disclosed by Bates et. al. in U.S. Pat. No. 8,080,034. The '034 device comprises an internal sealing surface pivoting on a rigid post to accommodate the longitudinal dimension of the seal inside the sheath ID. The exterior seal (second clamping member) is slidable along the rigid post and pivotal such that it, along with the internal seal, sandwiches the wall of the blood vessel via a locking ratchet. One problem with this design is that the pivoting feature increases the cross-sectional dimension of the seal thus requiring a larger diameter sheath than would be otherwise needed. In addition, the pivoting internal seal has no means to assure that the seal pivots to the correct sealing position as the ratchet closes. This could cause the internal seal to exit the blood vessel in the collapsed configuration as the user withdraws the deploying device. In addition no specific mechanism for the release of the seals from the deployment instrument is disclosed, other than a general statement "any known means."

The seals are released by the user cutting the suture thread in the device described in U.S. Pat. No. 6,045,569.

It is known that the opening in the blood vessel closes to some extent after the sheath is removed, thus allowing smaller seal surfaces than would otherwise be required. What is less known is that the opening does not close as quickly as a truly elastic material such as natural rubber or latex. For this reason, seal surfaces of closure devices that are activated in less than a second, or perhaps even longer, after sheath removal must be physically larger than the sheath outside diameter to avoid embolization of the seals because of the delayed blood vessel closure. The design of seals that are deployed through a sheath ID with dimensions larger than the sheath OD upon deployment is a challenge since the preferred material for seals are bio-absorbable and thus have limited mechanical properties.

An active sealing assembly comprising solid, flat interior and exterior elements that sandwich the blood vessel wall to insure hemostasis and yet have major dimensions that exceed the interior diameter of the introducer sheath to compensate for slow, partial closure of the wound upon removal of the sheath thereby minimizing leakage and avoiding embolization of the sealing components offers a design challenge. Components can be introduced through the sheath internal diameter (ID) longitudinally and rotated into a position adjacent to the blood vessel wall such that the longitudinal dimension exceeds the sheath ID with little or no concern regarding the mechanical properties of the material. The devices in the '461 and '034 patents are examples. As noted previously, these solutions have severe limitations.

Another method of accomplishing the desired result of obtaining a deployed seal larger than the sheath ID is to fold the seal elements while they traverse the sheath ID and reopen them upon deployment. Optimally, the major dimension of the seal elements should be 1.5 to 2 times larger than the outside diameter of the sheath. The '569 patent discloses an external seal made of an elongated pliable collagen plug that swells upon absorbing blood leaking from the wound and is tamped into more or less of a ball larger than the opening of the wound. The internal seal is inserted longitudinally through a special sheath which, with the aid of an attachment thread, rotates the seal parallel to the blood vessel surface.

The '569 device requires removing the catheter sheath and replacing it with a custom sheath prior to deployment, resulting in additional blood loss. The tamping force used to deploy the collagen against the anchor is left to the surgeon's feel, sometimes resulting in inadequate deployment and other times resulting in the collagen being pushed through the puncture wound and into the blood vessel along with the anchor. Inadequate tamping results in excessive bleeding with the potential for painful hematoma and over tamping can require a surgical procedure to remove the device from the blood vessel lumen. In addition, the absorption rate of the suture, the collagen, and the anchor may be different owing to the fact that they are formed from different materials, sometimes resulting in the premature detachment of the anchor, which can move freely in the blood stream and become lodged in the lower extremities of the body, again requiring surgical removal.

U.S. Pat. No. 5,350,399 discloses umbrella-shaped foldable bio-compatible seals that are not bioabsorbable.

It would be desirable therefore to provide a vessel-sealing device that actually seals the blood vessel and does not rely on the clotting of the blood. It is also desirable to provide a closure device that is deployable through the catheter sheath with minimal steps requiring less than 2 minutes for hemostasis. It would be also desirable to provide a reliable, active vessel-sealing device comprising a bio-absorbable seal assembly with deployed major dimensions larger than the sheath outside diameter.

SUMMARY OF THE INVENTION

Disclosed herein is seal assembly for sealing an opening in the wall of a blood vessel, the blood vessel having an interior wall surface, exterior wall surface, and a lumen, the seal assembly includes a first sealing element for placing inside the lumen of the blood vessel and to engage the interior wall surface thereof, a shaft integrally formed with the first sealing element and fixed in a predetermined configuration relative to the first sealing element, the rigid shaft having a length sufficient to extend through the opening of the blood vessel and at least a portion of any overlying tissue, an outer floating element slidingly movable along the shaft, and a second sealing element, the second sealing element slidingly movable relative to the first sealing element along the shaft to engage the outer floating element and position the outer floating element against the exterior surface and the first sealing element against the interior surface of the blood vessel to seal the opening in the blood vessel.

In some embodiments, first sealing element has an proximally facing surface lying in a first plane and the second sealing element has a distally facing surface lying in a second plane, the proximally facing surface engaging the interior wall surface and the distally facing surface engaging the exterior wall surface when deployed, the first plane and the second plane being parallel to one another.

In some embodiments, the shaft has at least two sides, the at least two sides being generally smooth and the outer floating element as an aperture to receive the shaft therethrough, the aperture generally being rectangular and having two generally smooth walls that correspond to the at least two generally smooth shaft walls to prevent rotation of the outer floating element relative to the shaft In some embodiments, the shaft has a reduced portion, the reduced portion having a cross section being smaller than a cross section of any other portion of the shaft.

In some embodiments, the first sealing element, the shaft, the outer floating element, and the second sealing element are made from a bio-absorbable material.

In other embodiments, the device includes a spacer disposed within the reduced portion, the spacer having a generally C-shaped configuration and prevents the shaft from bending about the reduced portion.

In still other embodiments, the device also includes an outer sleeve, the outer sleeve having a front end, back end, and an passageway extending therebetween, the passageway configured to retain the first sealing element, the shaft, the outer floating element, and the second sealing element, the passageway making contact with a top portion of a front end of the first sealing element and a bottom portion of back end of the first sealing element, thereby stressing the sealing assembly and aligning it within the passageway to pass through a sheath valve.

In another aspect, the present invention is directed to a seal assembly for sealing an opening in the wall of a blood vessel, the blood vessel having an interior wall surface, exterior wall surface, and a lumen, the seal assembly includes a first sealing element for placing inside the lumen of the blood vessel and to engage the interior wall surface thereof, a shaft integrally formed with the first sealing element and fixed in a predetermined configuration relative to the first sealing element, the rigid shaft having a length sufficient to extend through the opening of the blood vessel and at least a portion of any overlying tissue and a reduced portion, the reduced portion have a cross section being smaller than a cross section of any other portion of the shaft, an outer floating element slidingly movable along the shaft, and a second sealing element, the second sealing element slidingly movable relative to the first sealing element along the shaft to engage the outer floating element and position the outer floating element against the exterior surface and the first sealing element against the interior surface of the blood vessel to seal the opening in the blood vessel, wherein the shaft breaks at the reduced portion as a result of a force exerted on the second sealing element, which in turn exerts a force on the outer floating element thereby pushing the second sealing element and the second sealing element against the blood vessel and the first sealing element.

In yet another aspect of the present invention, a method is provided, the method includes providing a seal assembly for sealing the opening in the blood vessel, the seal assembly operatively connected to an insertion device and comprising a first sealing element for placing inside the lumen of the blood vessel and to engage the interior wall surface thereof, a shaft integrally formed with the first sealing element and fixed in a predetermined configuration relative to the first sealing element, the rigid shaft having a length sufficient to extend through the opening of the blood vessel and at least a portion of any overlying tissue, an outer floating element slidingly movable along the shaft, and a second sealing element, the second sealing element slidingly movable relative to the first sealing element along the shaft to engage the outer floating element and position the outer floating element against the exterior surface and the first sealing element against the interior surface of the blood vessel to seal the opening in the blood vessel, inserting a portion of the seal assembly into the lumen of the blood vessel, retracting the seal assembly and insertion device until the first seal element engages the interior wall surface of the blood vessel and causes the insertion device to automatically actuate thereby pushing the second sealing element and the outer floating element toward the exterior wall surface position the outer floating element against the exterior surface and causing the shaft to break at a reduced portion disposed within the shaft.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description of the present embodiments of the invention are intended to provide an overview or framework for understanding the nature and character of the invention as it is claimed. The accompanying drawings are included to provide a further understanding of the invention and are incorporated into and constitute a part of this specification. The drawings illustrate various embodiments of the invention and, together with the description, serve to explain the principles and operations of the invention.

BRIEF DESCRIPTION OF THE DRAWINGS

FIG. 4A is a cross section view along a longitudinal axis of a second sealing element of the seal assembly of FIG. 2;

FIG. 4B is a cross section view of the second sealing element of the seal assembly of FIG. 2 that is orthogonal to the view in FIG. 2;

DETAILED DESCRIPTION OF THE PREFERRED EMBODIMENTS

Figure 1:
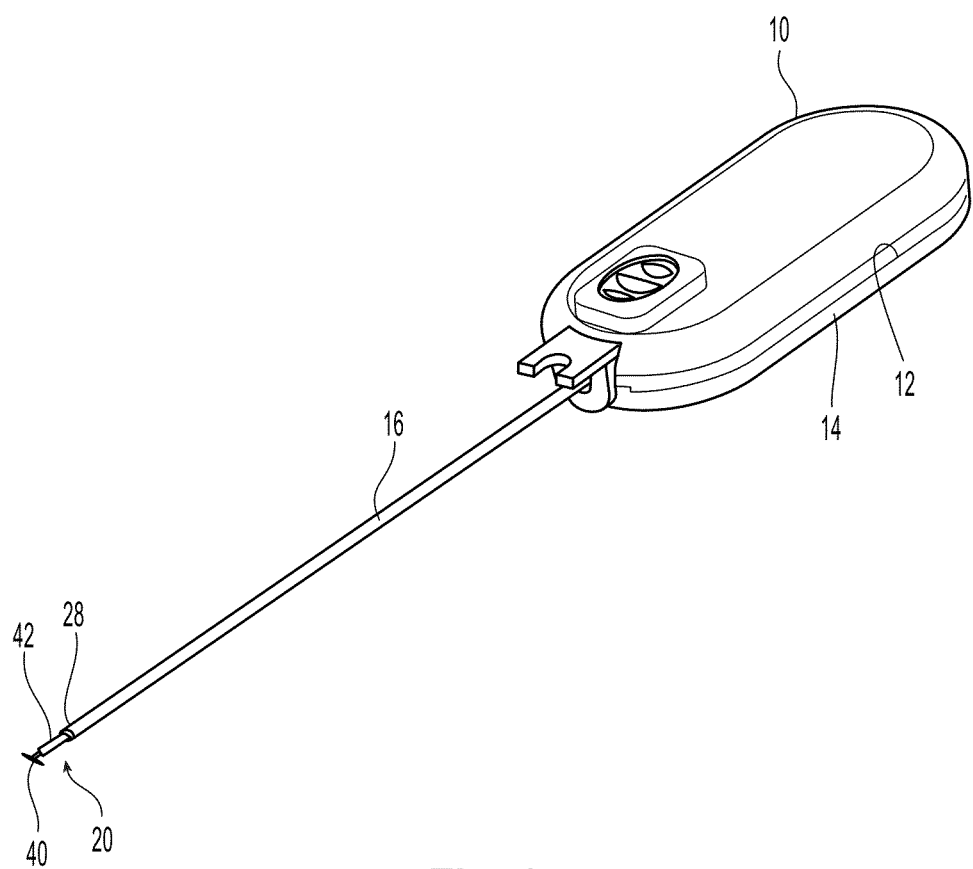
FIG. 1 is a perspective view of one embodiment of a sealing device according to the present invention.

Reference will now be made in detail to the present preferred embodiment(s) of the invention, examples of which are illustrated in the accompanying drawings. Whenever possible, the same reference numerals will be used throughout the drawings to refer to the same or like parts.

Figure 2:
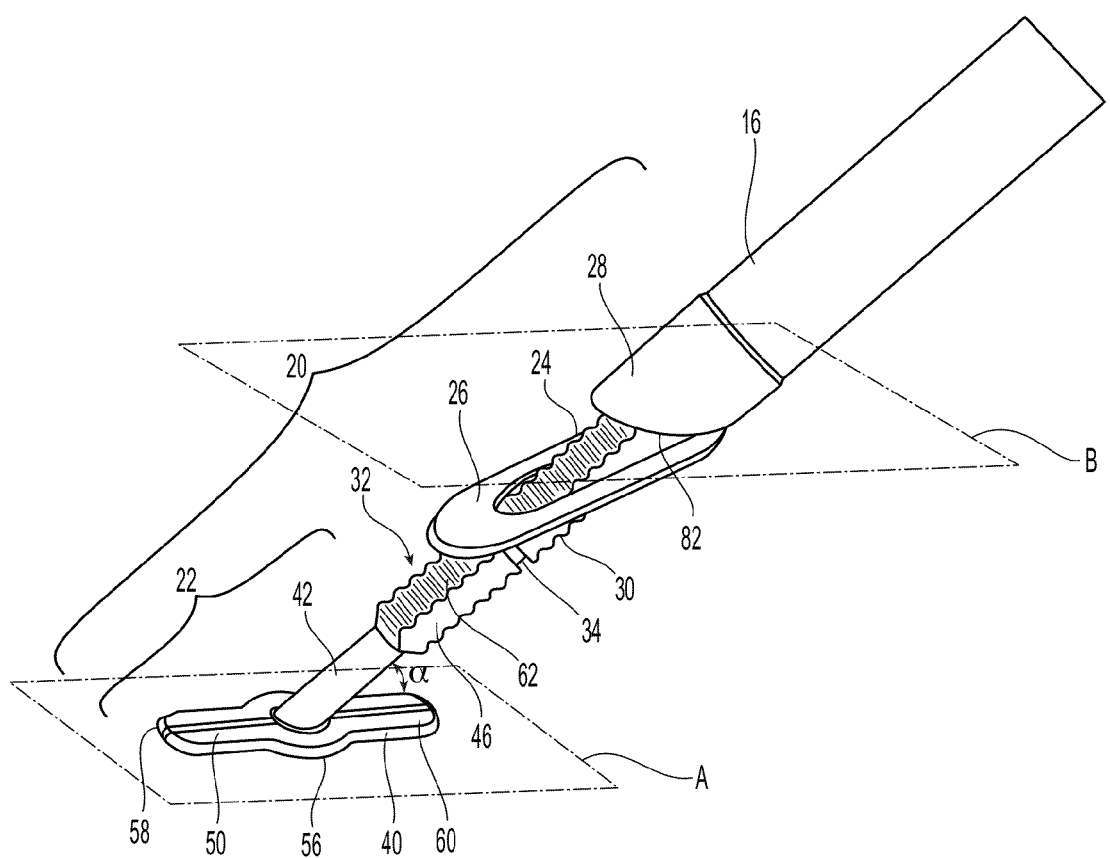
FIG. 2 is a perspective view of a portion of the sealing device of FIG. 1 illustrating the seal assembly thereof.

Referring to FIGS. 1 and 2, closure device 10 comprises two handle halves 12,14 housing an automatic mechanism detailed in co-pending application titled "Vessel Sealing Device with Automatic Deployment," assigned Ser. No. 13/746,276, the contents of which are incorporated herein by reference in their entirety. The automatic mechanism is coupled to the seal assembly 20 by a flexible pusher 16 and a flexible shaft 18. See also FIG. 6. Seal assembly 20 has a first sealing element 22, a knobbed rigid shaft 24, an outer floating element 26, and a second sealing element 28. Knobbed, rigid shaft 24 has a proximal section 30 and a distal section 32 separated by a weakened notch feature 34, which is configured to separate seal assembly 20 from the rest of the closure device 10 once the automatic deployment and sealing process is complete. The length of the distal section 32 of knobbed shaft 24 is dictated by the thickness of the vessel wall that can be accommodated (see FIG. 10). The first sealing element 22 also has a distal section 40 configured to interface with the inside wall of a vessel to be sealed (see also FIG. 9), a knobbed, rigid distal shaft section 32 (which is a part of the knobbed, rigid shaft 24), and ankle section 42 joining the distal section 40 to the knobbed, rigid distal shaft section 32. The ankle section 42 is attached to distal section 40 at an angle ∝, which is preferably at an angle of about 45°. Although other angles may be used, the value of angle ∝ may cause other values of the seal assembly to be changed, as discussed in detail below.

A more detailed view of the first sealing element 22 and the knobbed rigid shaft 24 are illustrated in FIGS. 3A-3D. The first sealing element 22 has the distal section 40, ankle section 42 and the knobbed, rigid distal shaft section 32. The distal section 40 has a proximal or top surface 50, a bottom surface 52 and an outer peripheral surface 56. The proximal or top surface 50 is preferably configured to engage the interior wall surface 142 of the blood vessel 140 (see FIG. 9), which means that the top surface 50 is preferably flat. However, the top surface 50 can be of any configuration (e.g., flat, convex, etc) and still come within the scope of the present invention. The bottom surface 52 is preferably flat, but may have other configurations. As noted below, the exact configuration of the surfaces 50,52 may also depend on the strain that is placed on them prior to and during insertion. The outer peripheral surface 56 is preferably continuous in that it has no discontinuities. That is, the outer peripheral surface 56 is smooth and has no sharp angles (e.g., 30, 45 or 90° angles). Since the distal section 40 is to be deformed prior to insertion into the blood vessel 140, any sharp angles tend to create stress points, potentially causing the distal section 40 to be bent/deflected beyond its ability to return to its original configuration. The distal section 40 has a thickness that increases from the front (or distal) end 58 to the rear (or proximal) end 60. In the embodiment illustrated in the figures, the thickness increases from 0.28 mm at the front end 58 to 0.30 mm at the rear end 60. However, other thicknesses and tapered shapes fall within the scope of the present invention.

Figure 3A:
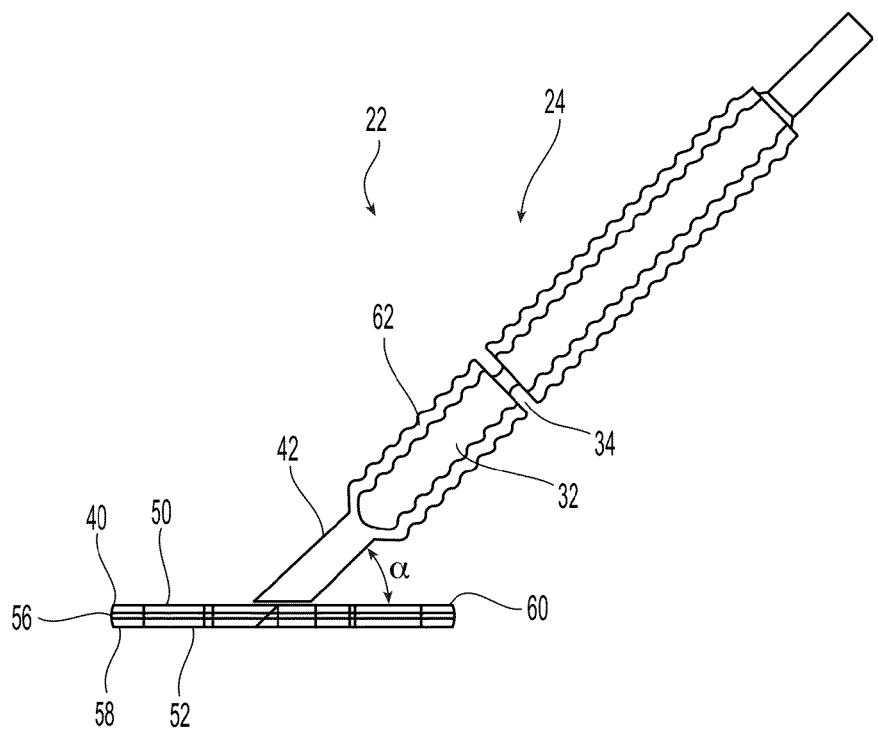
FIG. 3A is a side plan view of the first sealing element and the shaft.
Figure 3B:
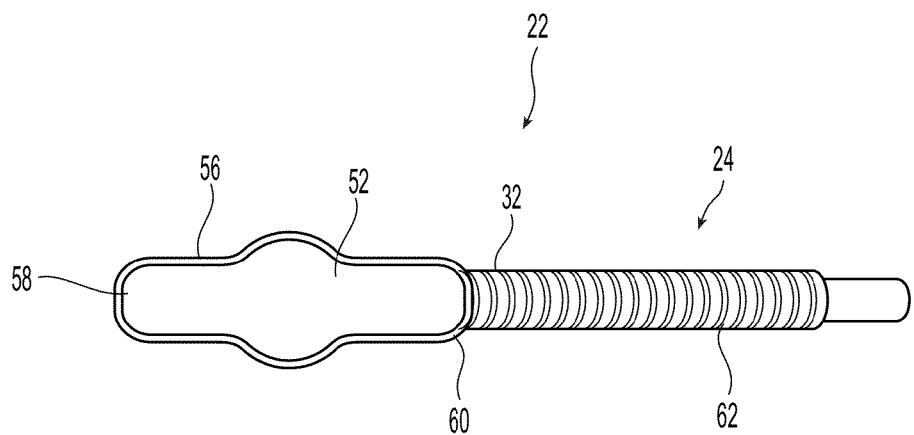
FIG. 3B is a bottom plan view of the first sealing element and the shaft.
Figure 3C:
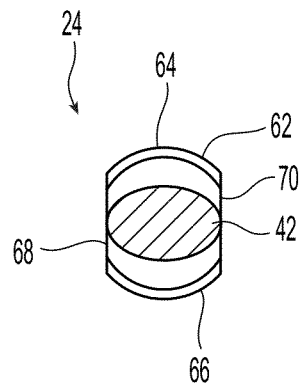
FIG. 3C is a cross section view of the shaft at the location of the reduced portion.
Figure 3D:
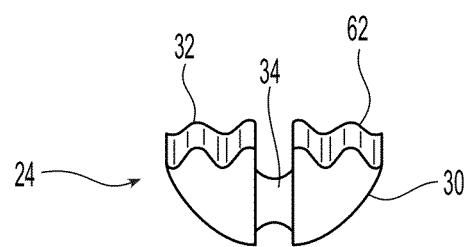
FIG. 3D is a partial side view of the shaft at the location of the reduced portion.

Illustrated in FIGS. 3C and 3D are a cross section of the knobbed rigid shaft 24 at the ankle 42 and partial side view of the knobbed rigid shaft 24 showing the weakened notch feature 34, respectively. The cross section of the ankle 42 in FIG. 3C illustrates the shape of the ankle 42, the knobs 62 on the upper 64 and the lower 66 surface, and the smooth sides 68,70 of the knobbed rigid shaft 24, which cooperates with the other portions of the first sealing element 22 to ensure that the outer floating element 26 and the second sealing element 28 are properly positioned, as discussed in more detail below.

Figure 6:
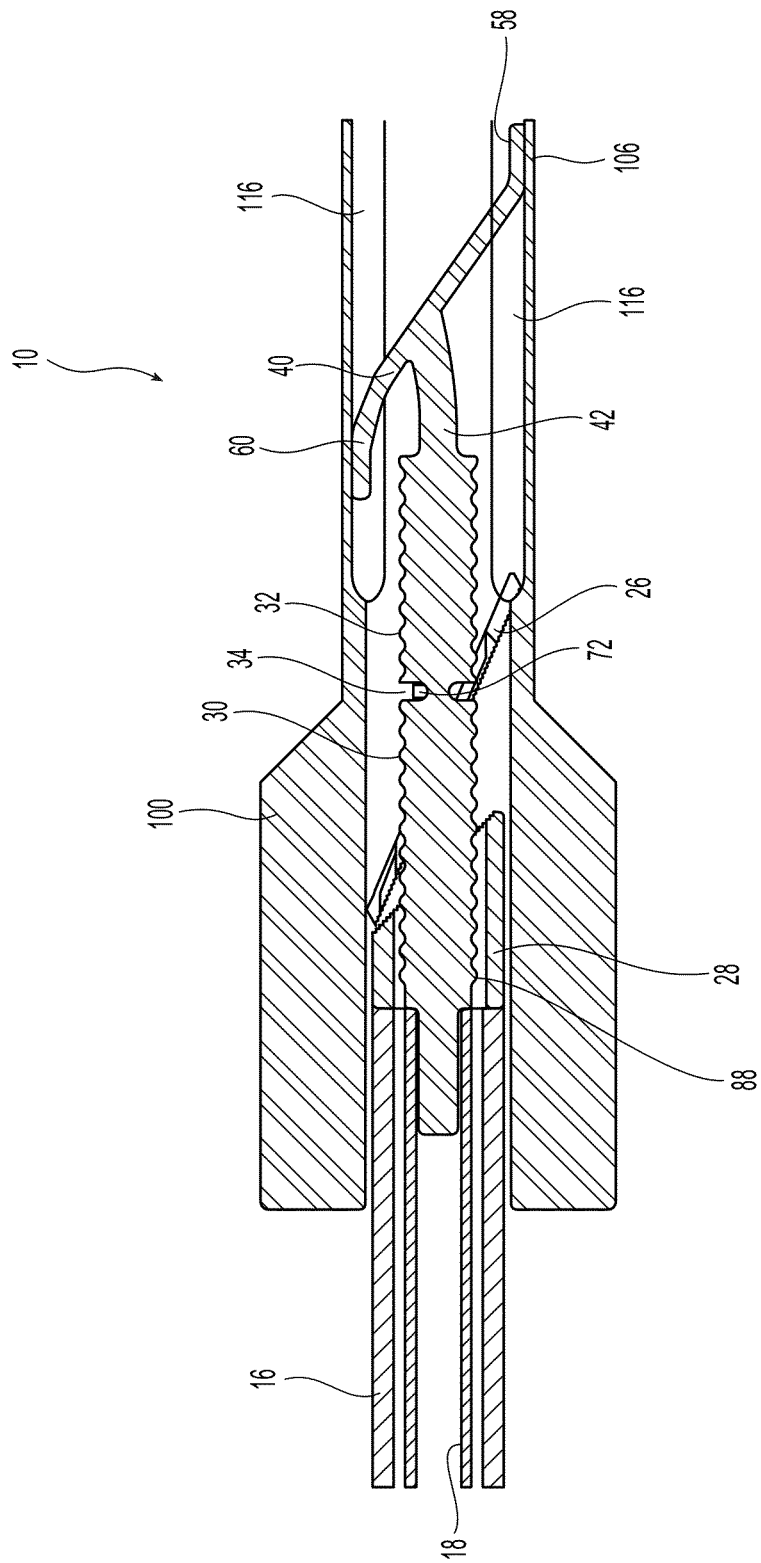
FIG. 6 is a cross section view of the seal assembly constrained in a sheath introducer.

The weakened notch feature 34 is illustrated in FIG. 3D. The weakened notch feature 34 has a smaller cross section than any other portion of the knobbed rigid shaft 24. This allows for the knobbed rigid shaft 24 to be broken at this point upon activation of the insertion device in the co-pending application by exerting a force in the direction of the length of the knobbed rigid shaft 24, causing the knobbed rigid shaft 24 to break at the weakened notch feature 34. In order to prevent the weakened notch feature 34 from breaking prematurely, a c-shaped ring 72 is clipped into the weakened notch feature 34, as illustrated in FIG. 6. The width of notch feature 34 is sized to equal the space between knobs 62 so that second seal 28 can easily transition over notch feature 34 upon automatic activation of device 10. The c-shaped ring 72 prevents the knobbed rigid shaft 24 from being tilted off center and breaking prematurely. The c-shaped ring 72 is preferably made from a bio-absorbable material since the c-shaped ring 72 can separate from both the proximal section 30 and the distal section 32 of the knobbed rigid shaft 24 upon breaking of the weakened notch feature 34 and there is no efficient way to retrieve it from the patient.

Second sealing element 28 is shown in more detail in FIGS. 4A and 4B. The second sealing element 28 has a proximally facing surface 80 and a sloped distally facing surface 82. An internal opening 84 defined by the internal surface 86 extends between the proximally facing surface 80 and the sloped distally facing surface 82. The internal surface 86 has extending therefrom and into the internal opening 84 projections 88 that interface with and engage the knobs 62 with an interference fit such that second sealing element 28 and knobbed rigid shaft 24 function as a one way latch assuring an adequate compression force regardless of the blood vessel wall thickness.

As can be best seen in FIG. 2, the proximal or top surface 50 of first sealing element 22 lies in a first plane A and the sloped distally facing surface 82 of second sealing element 28 lies in a second plane B. Preferably, the first plane A and the second plane B are parallel to one another.

Referring to FIG. 4B, the internal opening 84 of second sealing element 28 (and floating foot 26) have two flat surfaces 90 on opposite sides of the internal opening 84 that interface with flat surfaces 68,70 of knobbed rigid shaft 24 to provide rotational stability of the seal assembly components 26,28 thus assuring that the sloped distally facing surface 82 and the fully deployed floating foot 26 remain parallel with the distal section 40 of the first sealing element 22 and the proximal or top surface 50 in particular.

Figure 5A:
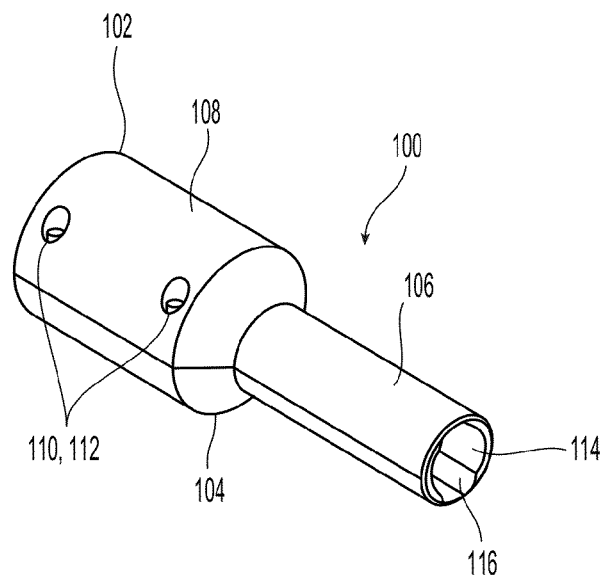
FIG. 5A is a perspective view of a sheath introducer used with the sealing device of FIG. 1.
Figure 5B:
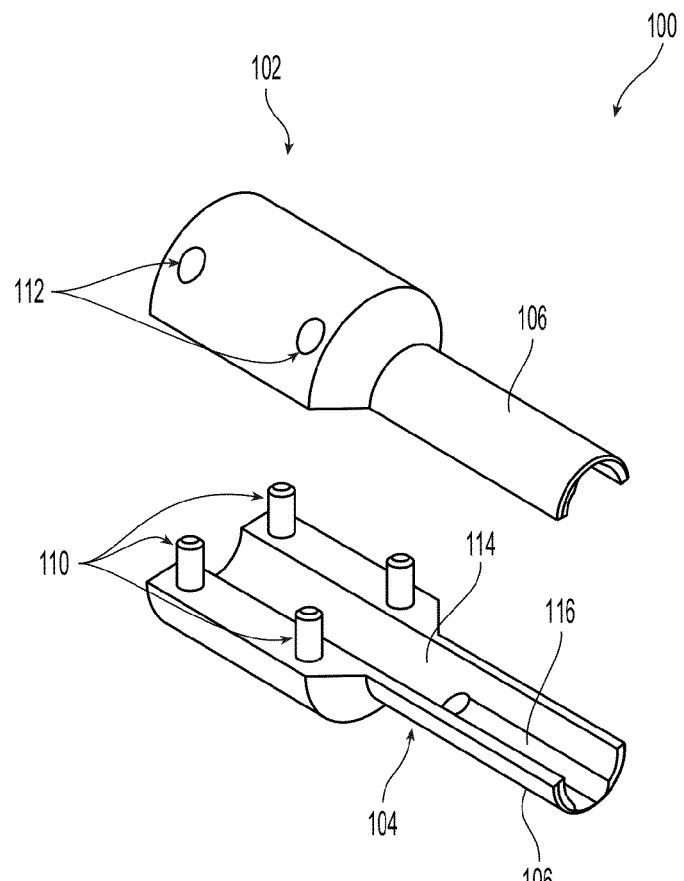
FIG. 5B is an exploded, perspective view of the sheath introducer of FIG. 5A.

FIGS. 5A and 6B depict introducer or outer sleeve 100, which is configured to protect seal assembly 20 from damage when inserting seal assembly 20 through a hemostatic valve, which, as discussed below and in more detail in the co-pending application, is one method in which the seal assembly is inserted into the patient. Introducer 100 comprises two halves, 102,104, which when assembled together form a generally cylindrical body having two different diameters. Front section 106 of introducer 100 has a smaller diameter than rear section 108. Front section 106 with the smaller diameter is configured to be inserted into hemostatic valve and rear section 108, having the larger diameter remains proximal to the hemostatic valve. While the two halves 102,104 can be assembled according to any typical manner, pins 110 on one of the two halves 102,104 are configured with a press fit into corresponding mating holes 112 thus holding halves 102,104 firmly together.

Figure 7:
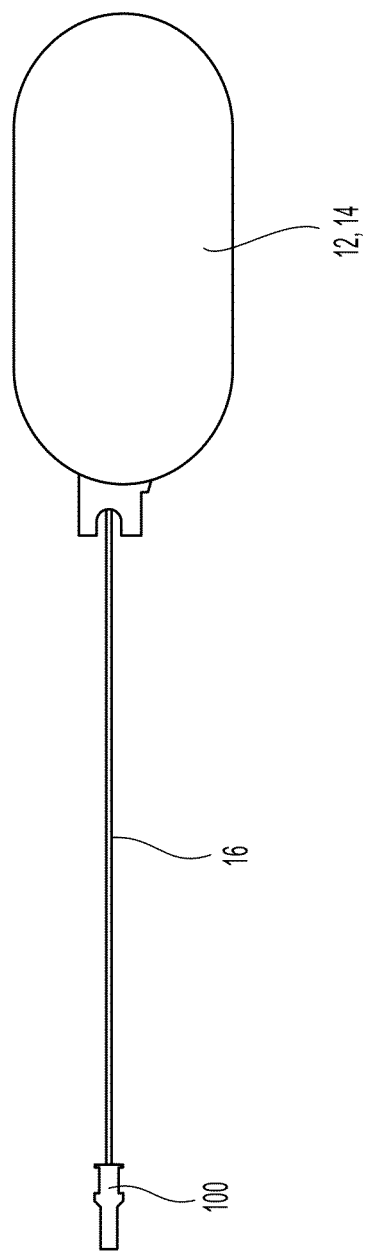
FIG. 7 is a top view of the sealing device with the sheath introducer of FIG. 5A.

The introducer 100 has an opening 114 that extends between the front section 106 and the rear section 108. However, within the opening 114 are also grooves 116 that are configured to accept seal assembly 20. The opening 114 is also configured to receive at least a portion of pusher 16 of the seal device 10. FIG. 6 is a cross section of seal assembly 20 in the initial position inside introducer 100 prior to insertion into a sheath 120. The front end 58 and the rear end 60 of the distal portion 40 of first sealing element 22 are deformed into a configuration such that the distal portion 40 of first sealing element 22 is able to pass through the inside dimension of cannula 122 upon insertion of closure device 10 resulting in the configuration shown in FIG. 6. The initial position of introducer 100 is shown in FIG. 7. After exit from distal end of cannula 122, the front end 58 and the rear end 60 of the distal portion 40 of first sealing element 22 return to the initial configuration as shown in FIG. 2 owing to the configuration shown in FIG. 6 not exceeding the elastic limit of the material from which the seal assembly 20 is constructed.

Figure 8:
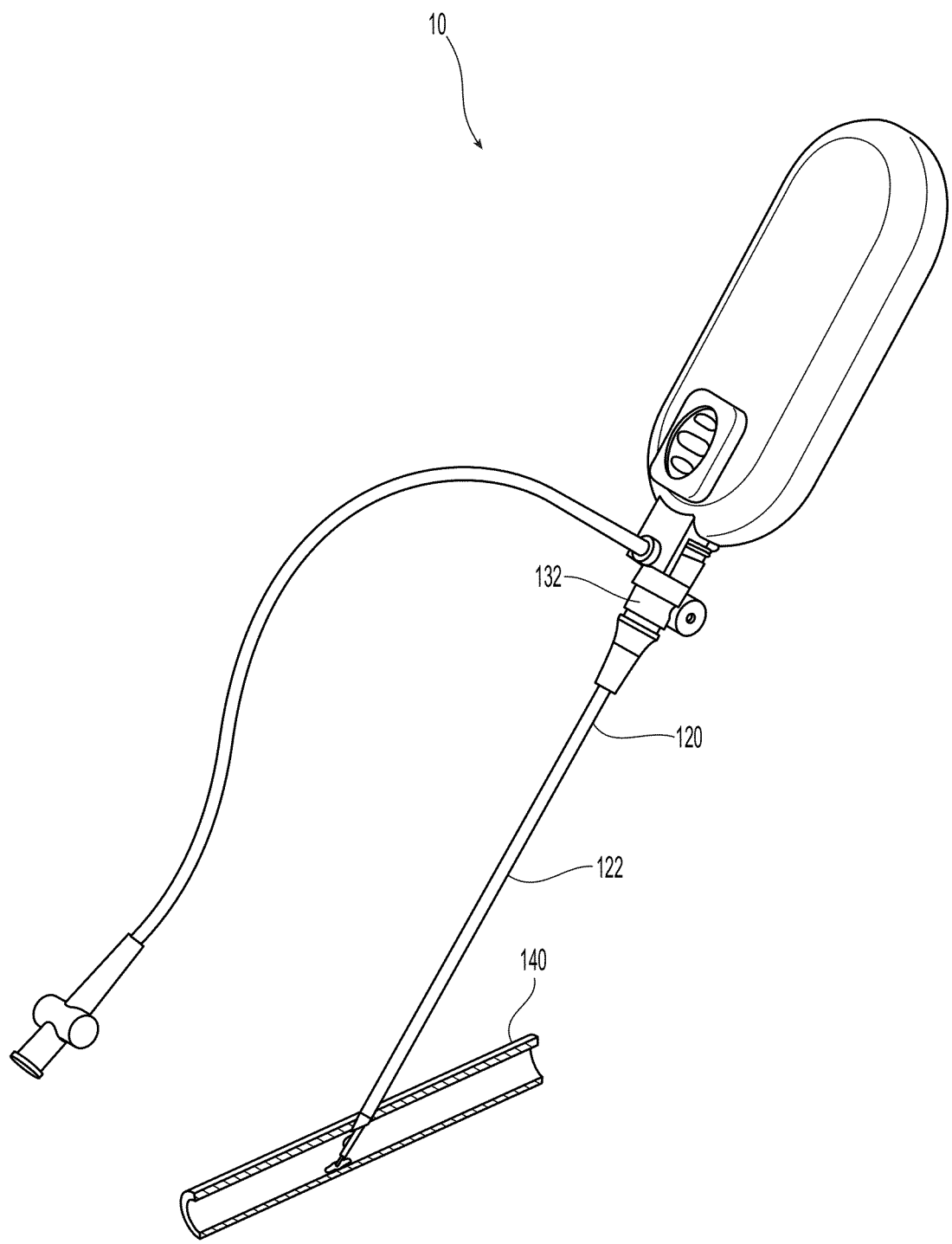
FIG. 8 is a perspective view of the sealing device inserted into a blood vessel.

FIG. 8 depicts closure device 10 inserted into sheath 120, the distal end of which is inside blood vessel 140. Proximal end of sheath 120 comprises hemostatic valve 132 attached to a funnel shaped section transitioning into cannula 122 at the distal end.

Figure 9:
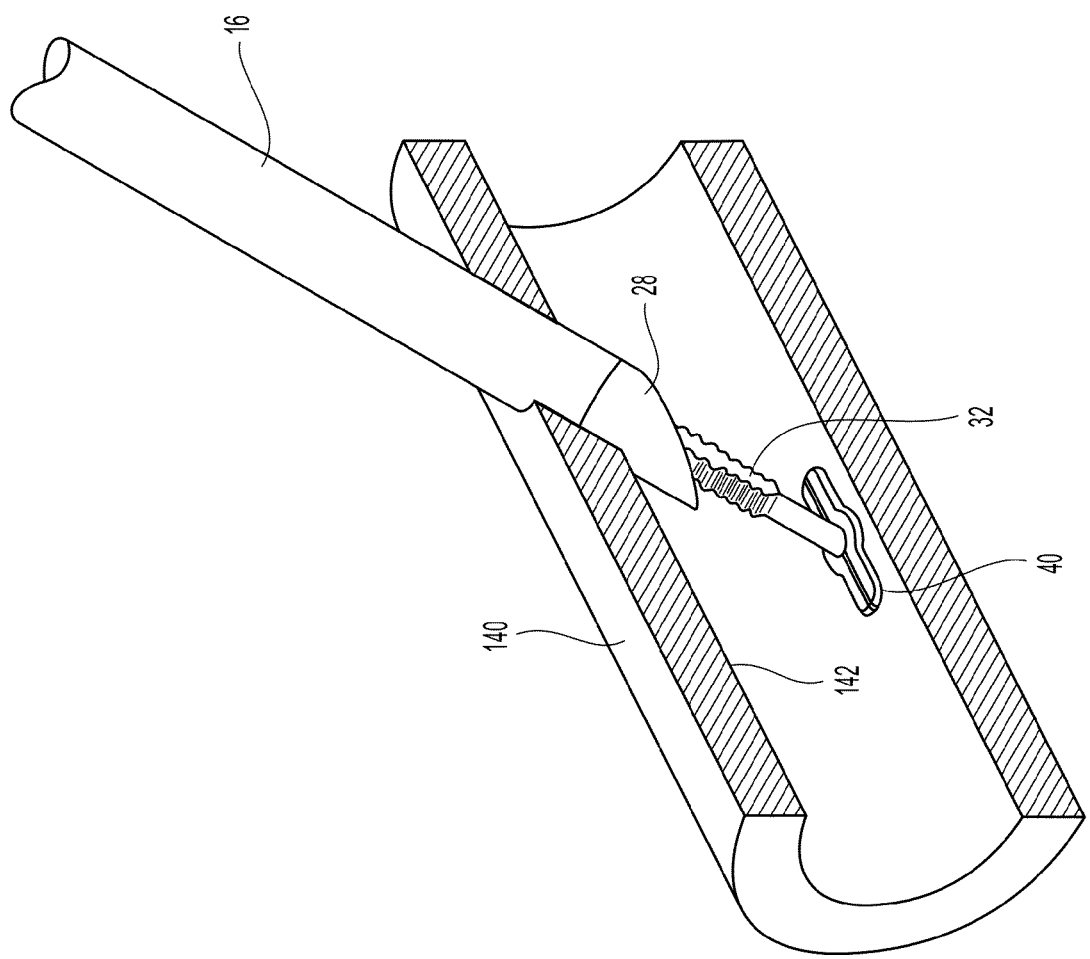
FIG. 9 is partial cross section view of a vessel with the sealing device inserted therein.
Figure 10:
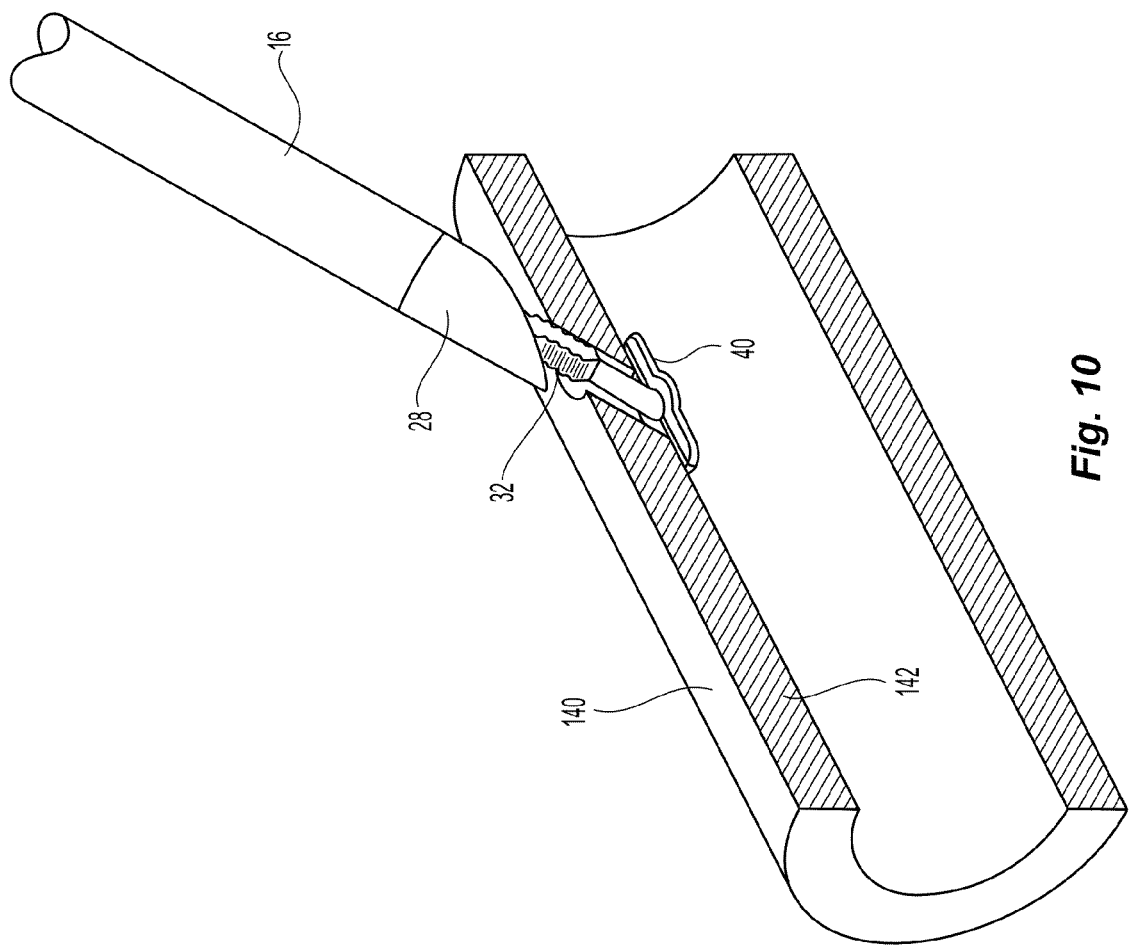
FIG. 10 is perspective view of the sealing device inserted into the blood vessel just before the sealing device is activated.
Figure 11:
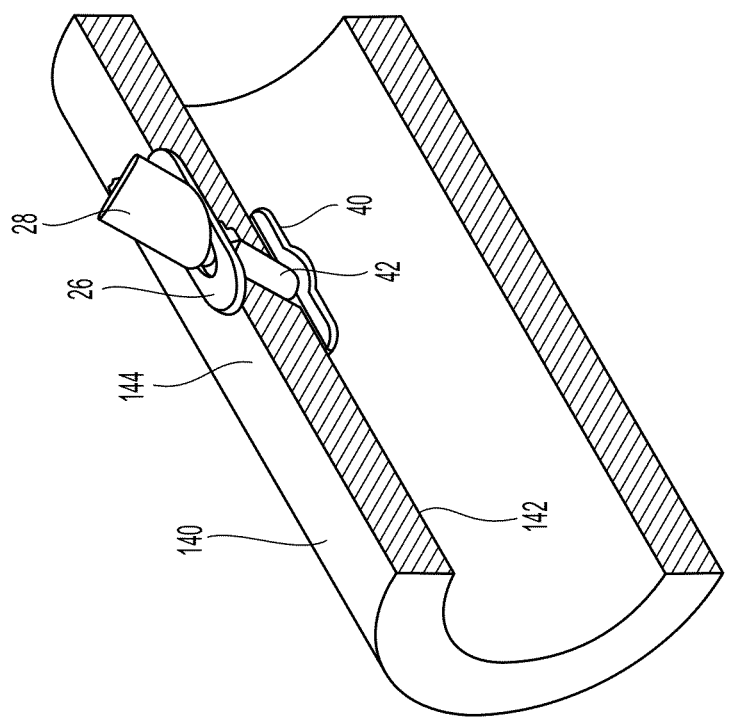
FIG. 11 is a perspective view of the seal assembly blocking the opening in the blood vessel after activation of the sealing device.

A method of using the current invention, in conjunction with FIGS. 9-11, is as follows: providing a sheath introducer 100 that surrounds and deforms seal assembly 20 such that seal assembly seal 20 can pass through sheath valve 132. See also FIGS. 6 & 8. Inserting pusher 16 through sheath 120, including valve 132 and cannula 122, causes at least a portion of seal assembly 20 to exit the distal end of cannula 122 and into blood vessel 140. A portion of the second sealing element 28 and the pusher 16 may be disposed within the blood vessel 140. See FIG. 10. Pulling on the closure device 10, the proximal or top surface 50 of the distal portion 40 of first sealing element 22 engages the interior blood vessel wall 142. This would also remove the second sealing element 28 and the pusher 16 from within the blood vessel 140. See FIG. 10. Continuing to pull on the sealing assembly 20 triggers an automatic mechanism in the closure device 10, which pushes pusher 16, and which in turn pushes second sealing element 28, and floating foot 26 (if present) distally such that floating foot 26 is in contact with outer wall of blood vessel 140. This will sandwich the second sealing element 28 against floating foot 26, blood vessel 140 and distal portion 40 of first sealing element 22 such that the opening in blood vessel 140 is hemostatically sealed, as shown in FIG. 11.

Figure 12:
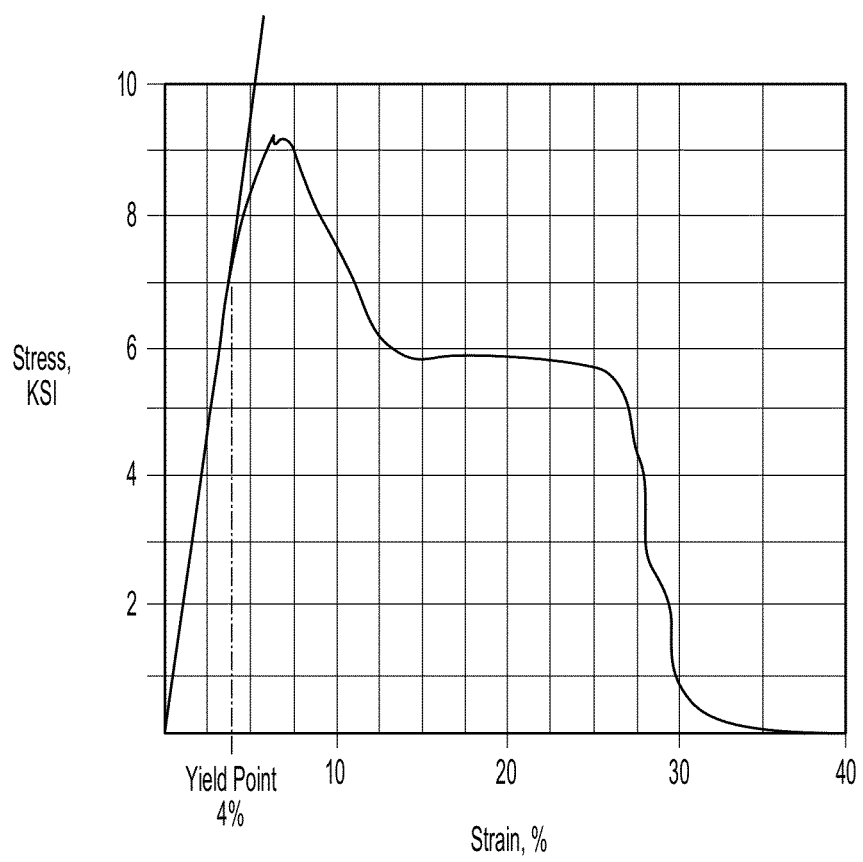
FIG. 12 is a stress-strain curve that illustrates the maximum strain without permanent deformation (yield point) is 4% for materials used in the seal assembly of FIG. 1.

To configure distal portion of first sealing element 22 such that the elastic limit of the bio-absorbable material is not exceeded when deformed in introducer 100 and deployed through cannula 122, material studies were undertaken. Bio-absorbable materials comprising different mole ratios of Lactide and Glycolide are commonly used for molded implant parts. These materials exhibit different properties such as glass transition temperature and absorption time; however the initial strength and flexibility are similar. As an example, molded samples 1.6 mm thick by 4 mm wide by 10 mm long of 85:15 L-Lactide:Glycolide with inherent viscosity of 2.1 dl/gm were tested in an Instron® Universal Tensile testing Machine Model 3340 according to ASTM E-8M-04 Standard at a crosshead speed of 2 inches/minute. A typical example of the stress strain curve is shown in FIG. 12. Of particular interest is the fact that the maximum strain without permanent deformation (yield point) is seen to be 4% for materials of this type and particularly for 85:15 L-Lactide:Glycolide with inherent viscosity of 2.1 dl/gm. Therefore, to assure no permanent deformation occurs for seal assembly 20 the maximum strain while undergoing insertion into the blood vessel through sheath 120 must be below 4%. It is worth noting that the yield point was independent of sterilization radiation level up to 50 KGy the maximum strain at break decreased with radiation level however.

Figure 13A:
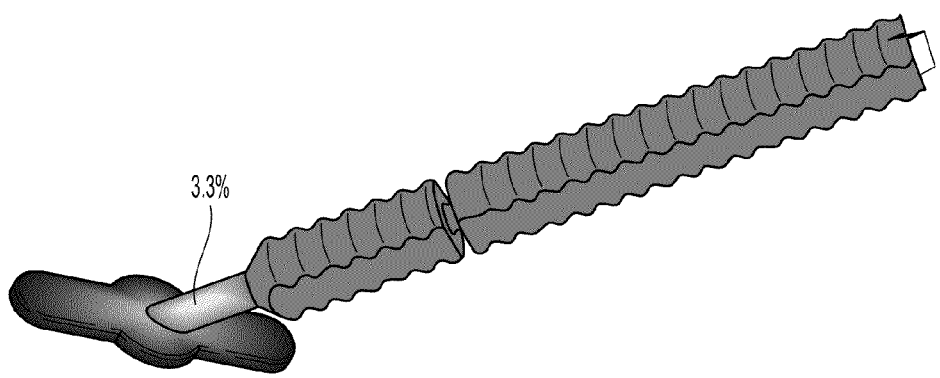
FIG. 13A illustrates a representation of strain that would be introduced into the first sealing element on the top side thereof if constrained in the sheath introducer of FIG. 5A.
Figure 13B:
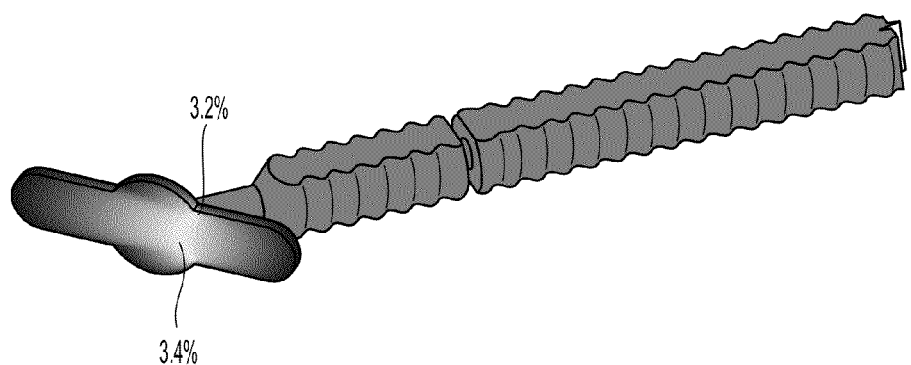
FIG. 13B illustrates a representation of strain that would be introduced into the first sealing element on the bottom side thereof if constrained in the sheath introducer of FIG. 5A.
Figure 13C:
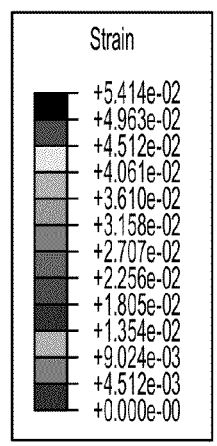
FIG. 13C is a legend for the strain representations of the first sealing element constrained in the introducer.

The strain induced into a sample under different stress loads is dependent on the material basic mechanical properties but as importantly the geometric configuration. From a practical stand point closure devices are most often used in 6 French or smaller sheaths for cardiac procedures and up to 18 French or larger for AAA procedures. It is noted that when the first sealing element 22 for a 6 French closure device, is molded from 85:15 L-Lactide:Glycolide with inherent viscosity of 2.1 dl/gm, the present design stays within the strain limits. In fact, Finite Element Analysis (FEA) of variations of the present design indicate that the continuous outer periphery and the thickness taper from 0.28 to 0.30 in distal portion of first sealing element 22, along with the oval configuration of ankle 42 are critical in keeping the strain below 4% in the deformed state inside introducer 100, given the overall size and shape of the sealing assembly. FIGS. 13A-C illustrate by a grayscale map the strain in sealing assembly 20 constrained in introducer 100. It can be seen that the maximum strain is below 4% for this configuration and material.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A seal assembly for sealing an opening in the wall of a blood vessel, the blood vessel having an interior wall surface, exterior wall surface, and a lumen, the seal assembly comprising:
    a first sealing element for placing inside the lumen of the blood vessel and to engage the interior wall surface thereof;
    a shaft integrally formed with the first sealing element and fixed in a predetermined configuration relative to the first sealing element, wherein the shaft and the first sealing element form a one single piece component, the shaft having a length sufficient to extend through the opening of the blood vessel and at least a portion of any overlying tissue;
    an outer floating element slidingly movable along the shaft; and
    a second sealing element, the second sealing element slidingly movable relative to the first sealing element along the shaft to engage the outer floating element and configured to position the outer floating element against the exterior wall surface and the first sealing element against the interior wall surface of the blood vessel to seal the opening in the blood vessel, and
    wherein the shaft has at least two sides, the at least two sides being generally smooth and the outer floating element has an aperture to receive the shaft therethrough, the aperture generally being rectangular and having two generally smooth walls that correspond to the at least two generally smooth shaft walls to prevent rotation of the outer floating element relative to the shaft.

2. The seal assembly for sealing an opening in the wall of a blood vessel according to claim 1, wherein the first sealing element has an proximally facing surface lying in a first plane and the second sealing element has a distally facing surface lying in a second plane, the proximally facing surface configured to engage the interior wall surface and the distally facing surface configured to engage the exterior wall surface when deployed, the first plane and the second plane being parallel to one another.

3. The seal assembly for sealing an opening in the wall of a blood vessel according to claim 1, wherein the shaft has four sides, two of the four sides having a plurality of equally spaced projections along a length thereof.

4. The seal assembly for sealing an opening in the wall of a blood vessel according to claim 1 wherein the first sealing element has a front end, a back end and a thickness, the thickness increasing from the front to the back end.

5. The seal assembly for sealing an opening in the wall of a blood vessel according to claim 4, wherein the thickness increases between 5 and 10 percent.

6. The seal assembly for sealing an opening in the wall of a blood vessel according to claim 4, wherein the thickness increases about 7 percent.

7. The seal assembly for sealing an opening in the wall of a blood vessel according to claim 1 wherein the first sealing element has an outer peripheral surface, the outer peripheral surface being continuous without any discontinuities.

8. The seal assembly for sealing an opening in the wall of a blood vessel according to claim 1, wherein the shaft has a reduced portion, the reduced portion having a cross section being smaller than a cross section of any other portion of the shaft.

9. The seal assembly for sealing an opening in the wall of a blood vessel according to claim 8, further comprising a spacer disposed within the reduced portion, the spacer having a generally C-shaped configuration and prevents the shaft from bending about the reduced portion.

10. The seal assembly for sealing an opening in the wall of a blood vessel according to claim 8, wherein the shaft breaks at the reduced portion as a result of a force exerted on the second sealing element, which in turn exerts a force on the outer floating element thereby pushing the second sealing element and the outer floating element against the blood vessel and the first sealing element.

11. The seal assembly for sealing an opening in the wall of a blood vessel according to claim 1, wherein the second sealing element has a first end having a distally facing surface and a second end opposite the first end and an opening extending therebetween, the opening having at least one projection extending from an inner wall into the opening to engage the projections on the shaft.

12. The seal assembly for sealing an opening in the wall of a blood vessel according to claim 11, wherein the opening in the second sealing element is defined by two generally planar walls, the two generally planar walls disposed on opposite sides of the opening and two generally curved walls, the generally curved walls on opposite sides of the opening, the two generally curved walls corresponding to the projections on the shaft.

13. The seal assembly for sealing an opening in the wall of a blood vessel according to claim 1, wherein the first sealing element, the shaft, the outer floating element, and the second sealing element are made from a bio-absorbable material.

14. The seal assembly for sealing an opening in the wall of a blood vessel according to claim 1, further comprising an outer sleeve, the outer sleeve having a front end, back end, and a passageway extending therebetween, the passageway configured to retain the first sealing element, the shaft, the outer floating element, and the second sealing element, the passageway making contact with a top portion of a front end of the first sealing element and a bottom portion of back end of the first sealing element, thereby stressing the sealing assembly and aligning it within the passageway to pass through a sheath valve.

15. The seal assembly for sealing an opening in the wall of a blood vessel according to claim 14, wherein the outer sleeve stresses the seal assembly by no more than 4%.

16. The seal assembly for sealing an opening in the wall of a blood vessel according to claim 1, wherein the shaft and the first sealing element are joined at an angle of about 45 degrees.

17. A seal assembly for sealing an opening in the wall of a blood vessel, the blood vessel having an interior wall surface, exterior wall surface, and a lumen, the seal assembly comprising:
   a first sealing element for placing inside the lumen of the blood vessel and to engage the interior wall surface thereof;
   a shaft integrally formed with the first sealing element and fixed in a predetermined configuration relative to the first sealing element, the shaft having a length sufficient to extend through the opening of the blood vessel and at least a portion of any overlying tissue and a reduced portion, the reduced portion have a cross section being smaller than a cross section of any other portion of the shaft;
   an outer floating element slidingly movable along the shaft; and
   a second sealing element, the second sealing element slidingly movable relative to the first sealing element along the shaft to engage the outer floating element and configured to position the outer floating element against the exterior wall surface and the first sealing element against the interior wall surface of the blood vessel to seal the opening in the blood vessel,
   wherein the shaft breaks at the reduced portion as a result of a force exerted on the second sealing element, which in turn exerts a force on the outer floating element thereby pushing the second sealing element and the second sealing element against the blood vessel and the first sealing element, and
   wherein the shaft has at least two sides, the at least two sides being generally smooth and the outer floating element has an aperture to receive the shaft therethrough, the aperture generally being rectangular and having two generally smooth walls that correspond to the at least two generally smooth shaft walls to prevent rotation of the outer floating element relative to the shaft.

18. The seal assembly for sealing an opening in the wall of a blood vessel according to claim 17, wherein the reduced portion is disposed between two of the plurality of equally spaced projections.

19. A method of sealing an opening in the wall of a blood vessel, the blood vessel having an interior wall surface, exterior wall surface, and a lumen, the method comprising the steps of:
   providing a seal assembly for sealing the opening in the blood vessel, the seal assembly operatively connected to an insertion device and comprising a first sealing element for placing inside the lumen of the blood vessel and to engage the interior wall surface thereof, a shaft integrally formed with the first sealing element and fixed in a predetermined configuration relative to the first sealing element, the shaft having a length sufficient to extend through the opening of the blood vessel and at least a portion of any overlying tissue, an outer floating element slidingly movable along the shaft, and a second sealing element, the second sealing element slidingly movable relative to the first sealing element along the shaft to engage the outer floating element and position the outer floating element against the exterior wall surface and the first sealing element against the interior wall surface of the blood vessel to seal the opening in the blood vessel;
   inserting a portion of the seal assembly into the lumen of the blood vessel; and
   retracting the seal assembly and insertion device until the first seal element engages the interior wall surface of the blood vessel and causes the insertion device to automatically actuate thereby pushing the second sealing element and the outer floating element toward the exterior wall surface position the outer floating element against the exterior surface and causing the shaft to break at a reduced portion disposed within the shaft.

* * * * *